United States Patent
Aoyama

(10) Patent No.: US 8,534,820 B2
(45) Date of Patent: Sep. 17, 2013

(54) INK FOR INK-JET RECORDING, INK CARTRIDGE, INK-JET RECORDING APPARATUS, METHOD OF DETERMINING, AND METHOD OF INK-JET RECORDING

(75) Inventor: Michiko Aoyama, Nagoya (JP)

(73) Assignee: Brother Kogyo Kabushiki Kaisha, Nagoya-shi, Aichi-ken (JP)

(*) Notice: Subject to any disclaimer, the term of this patent is extended or adjusted under 35 U.S.C. 154(b) by 757 days.

(21) Appl. No.: 12/357,341

(22) Filed: Jan. 21, 2009

(65) Prior Publication Data
US 2009/0186155 A1    Jul. 23, 2009

(30) Foreign Application Priority Data
Jan. 21, 2008   (JP) .................. 2008-010070

(51) Int. Cl.
*B41J 2/01*    (2006.01)
(52) U.S. Cl.
USPC .......................................... 347/100; 347/101
(58) Field of Classification Search
USPC ............ 347/100, 95, 96, 102, 101; 106/31.6, 106/31.13, 31.27; 523/160
See application file for complete search history.

(56) References Cited

U.S. PATENT DOCUMENTS

| | | | |
|---|---|---|---|
| 5,286,286 A * | 2/1994 | Winnik et al. ................ | 347/100 |
| 5,421,869 A * | 6/1995 | Gundjian et al. .......... | 106/31.19 |
| 5,542,971 A * | 8/1996 | Auslander et al. ............ | 347/107 |
| 6,106,110 A * | 8/2000 | Gundjian et al. ................ | 347/98 |
| 2006/0017767 A1* | 1/2006 | Matsuzawa et al. ............ | 347/21 |
| 2006/0234018 A1* | 10/2006 | Nagashima et al. ....... | 428/195.1 |
| 2007/0119951 A1* | 5/2007 | Auslander et al. ............ | 235/491 |
| 2009/0246765 A1* | 10/2009 | Suita ............................... | 435/6 |

FOREIGN PATENT DOCUMENTS

| | | | |
|---|---|---|---|
| JP | 09227817 A | * | 9/1997 |
| JP | H09-227817 A | | 9/1997 |
| JP | 2000-226544 A | | 8/2000 |
| JP | 2002-137531 A | | 5/2002 |

* cited by examiner

*Primary Examiner* — Manish S Shah
(74) *Attorney, Agent, or Firm* — Baker Botts L.L.P.

(57) ABSTRACT

An ink for ink-jet recording includes a luminescence marker which emits light by oxidization. It may be determined whether the ink for ink-jet recording is used for recording the ink-jet recorded object with a simple method such as an evaluation of luminescence by oxidation, without requiring a special equipment.

7 Claims, 2 Drawing Sheets (A)

(B)

(C)

INK FOR INK-JET RECORDING, INK CARTRIDGE, INK-JET RECORDING APPARATUS, METHOD OF DETERMINING, AND METHOD OF INK-JET RECORDING

CROSS-REFERENCE TO RELATED APPLICATION

This application claims priority from Japanese Patent Application No. 2008-010070 filed on Jan. 21, 2008. The entire subject matter of the Japanese Patent Application is incorporated herein by reference.

BACKGROUND

1. Field

The present invention relates to an ink for ink-jet recording, an ink cartridge, an ink-jet recording apparatus, a method of determining, and a method of ink-jet recording.

2. Description of the Related Art

Conventionally, in order to apply a fluorescence emission marker on an ink-jet recorded object, an ink for ink-jet recording, in which a fluorescence substance that emits fluorescence by absorbing an ultraviolet ray is blended, is widely used. Further, an ink for ink-jet recording, which contains a fluorescence substance that rarely emits fluorescence by absorbing a visible ray whose wavelength is 400 nm to 600 nm and emits fluorescence by absorbing a near-infrared ray whose wavelength is 650 nm to 900 nm, is proposed (Japanese Patent Application Laid-open No. H09-227817). The ink-jet recorded object recorded using the aforementioned ink rarely emits light in a case where the visible ray is irradiated, and emits light in a case where the near-infrared ray is irradiated. The fluorescence substance serves as a marker for preventing forgery of the ink-jet recorded object such as a gift certificate, a postcard, an envelope, a check, an identification card, a ticket, a bond, and the like.

SUMMARY

An ink for ink-jet recording comprises a luminescence marker which emits light by oxidization.

An ink cartridge comprises an ink for ink-jet recording and the ink is the ink for ink-jet recording comprising the luminescence marker.

An ink-jet recording apparatus comprises an ink storing portion and an ink ejecting unit. An ink stored in the ink storing portion is ejected by the ink ejecting unit. The ink cartridge is stored in the ink storing portion.

A first method of determining is a method of determining an ink for ink-jet recording used for recording an ink-jet recorded object. The determination determines whether the ink is an ink for ink-jet recording comprising a luminescence marker which emits light by oxidization. A whole or a part of a recording part of the ink-jet recorded object is oxidized. In a case where the recording part emits light by oxidation, it is determined that the ink is the ink for ink-jet recording comprising the luminescence marker which emits light by oxidization. In a case where the recording part does not emit light by oxidation, it is determined that the ink is not the ink for ink-jet recording comprising the luminescence marker which emits light by oxidization.

A method of ink-jet recording performs recording by ejecting an ink by an ink-jet recording system relative to a recording medium. The ink comprises a clear ink comprising a luminescence marker which emits light by oxidization. A determining part is formed by ejecting the clear ink on a part different from a recording part of the recording medium.

A second method of determining is a method of determining an ink for ink-jet recording used for recording an ink-jet recorded object. The determination determines whether the clear ink used for forming the determining part of the recording medium recorded by the method of ink-jet recording is a clear ink comprising a luminescence marker which emits light by oxidization. A whole or a part of the determining part of the recording medium is oxidized. In a case where the determining part emits light by oxidation, it is determined that the clear ink is the clear ink comprising the luminescence marker which emits light by oxidization. In a case where the determining part does not emit light by oxidation, it is determined that the clear ink is not the clear ink comprising the luminescence marker which emits light by oxidization.

DETAILED DESCRIPTION

Figure 1:
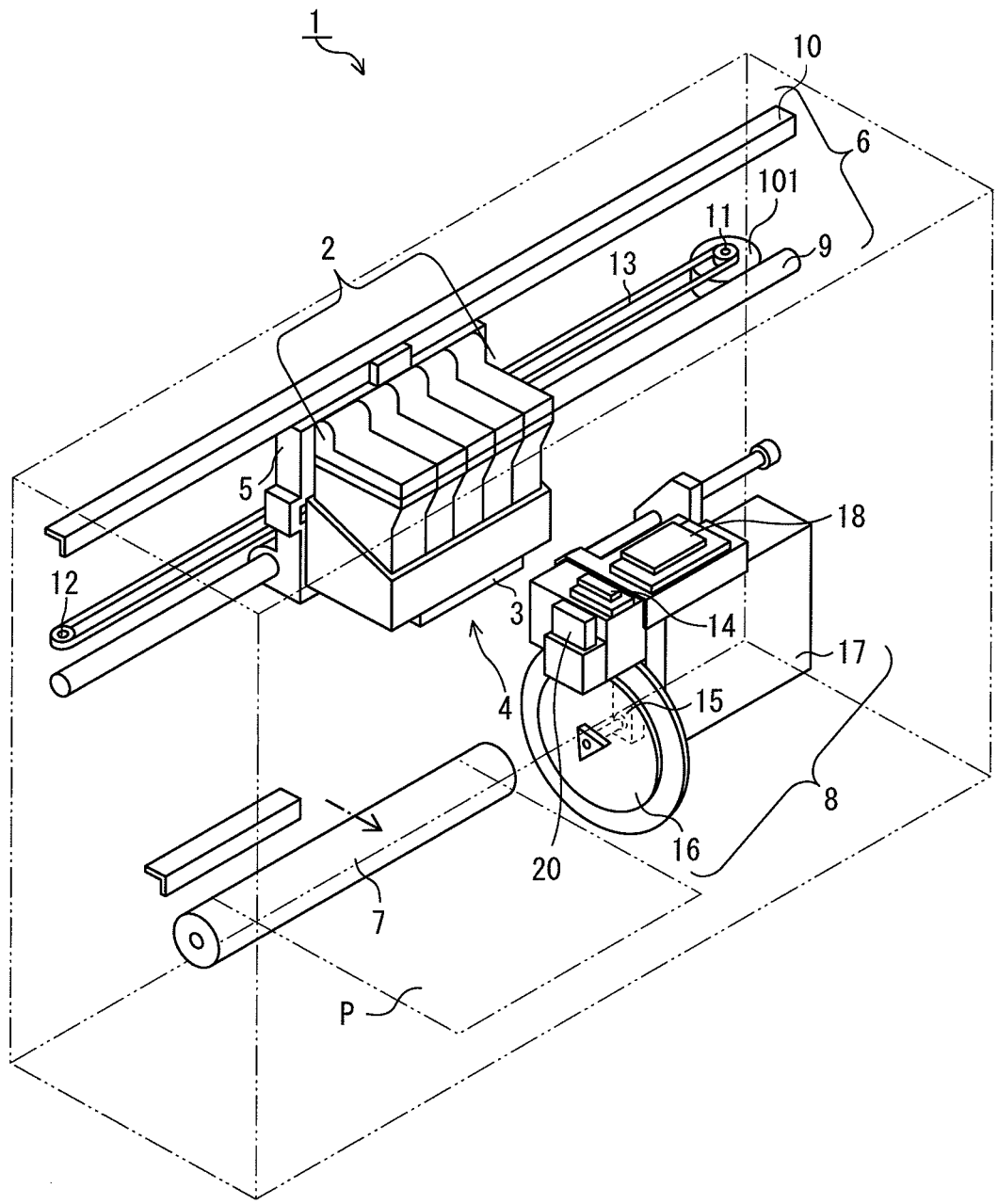
FIG. 1 is a schematic perspective view showing a construction of an example of an ink-jet recording apparatus.

First, the ink for ink-jet recording is explained. The ink for ink-jet recording (hereinafter, also may simply be referred to as "ink") comprises a luminescence marker that emits light by oxidation (hereinafter, also may simply be referred to as "luminescence marker"). Composition of the ink for ink-jet recording is not limited as long as it comprises the luminescence marker. Examples of the ink for ink-jet recording include a water-based ink, an oil-based ink, and the like. The ink for ink-jet recording is preferably a water-based ink comprising water and water-soluble organic solvent.

The water may be ion-exchange water or purified water. A ratio of the water relative to the total amount of the ink is, for example, in the range of about 10 wt % to about 90 wt %, and in the range of about 40 wt % to about 80 wt %. The ratio of the water may be a balance of the other components, for example.

The water-soluble organic solvent is classified into a humectant and a penetrant. The humectant prevents ink from drying at a tip of an ink-jet head, for example. The penetrant adjusts a drying rate of ink on a recording medium, for example.

The humectant is not particularly limited. Examples of the humectant include lower alcohol such as methyl alcohol, ethyl alcohol, n-propyl alcohol, isopropyl alcohol, n-butyl alcohol, sec-butyl alcohol, tert-butyl alcohol, and the like; polyalcohol such as 1,3-butanediol, 1,5-pentanediol, 1,6-hexanediol, glycerin, 1,2,6-hexanetriol, 1,2,4-butanetriol, 1,2,3-butanetriol, pentanetriol, alkylene glycol, polyalkylene glycol, and the like; amide such as formamide, N-methyl formamide, N,N-dimethyl formamide, dimethylacetamide, and the like; amine such as monoethanolamine, diethanolamine, triethanolamine, monoethylamine, diethylamine, triethylamine, and the like; ketone such as acetone, and the like; ketoalcohol such as diacetone alcohol, and the like; ether such as tetrahydrofuran, dioxane, and the like; 2-pyrrolidone; N-methyl-2-pyrrolidone; N-hydroxyethyl-2-pyrrolidone; nitrogen-containing heterocyclic compound such as 1,3-dimethyl-2-imidazolidinone, ε-caprolactam, and the like; sulfur-containing compound such as dimethylsulfoxide, sulfolane, thiodiethanol, and the like; and the like. Examples of the alkylene glycol include, without limitation, ethylene glycol, diethylene glycol, triethylene glycol, propylene glycol, dipropylene glycol, tripropylene glycol, butylene glycol, thiodiglycol, hexylene glycol, and the like. Examples of the polyalkylene glycol include, without limitation, polyethylene glycol, polypropylene glycol, and the like. Among them, polyalcohol such as glycerin and alkylene glycol is preferable. One of the humectants may be used alone or two or more of them may be used in combination.

A ratio of the humectant (humectant ratio) relative to the total amount of the ink is not particularly limited and is, for example, in the range of about 0 wt % to about 95 wt %, in the range of about 10 wt % to about 80 wt %, and in the range of about 10 wt % to about 50 wt %.

The penetrant is not particularly limited and examples thereof include ethylene glycol methyl ether, ethylene glycol ethyl ether, ethylene glycol-n-propyl ether, ethylene glycol-n-butyl ether, diethylene glycol methyl ether, diethylene glycol ethyl ether, diethylene glycol-n-propyl ether, diethylene glycol-n-butyl ether, diethylene glycol dimethyl ether, diethylene glycol diethyl ether, diethylene glycol dipropyl ether, diethylene glycol dibutyl ether, triethylene glycol methyl ether, triethylene glycol ethyl ether, triethylene glycol-n-propyl ether, triethylene glycol-n-butyl ether, triethylene glycol dimethyl ether, triethylene glycol diethyl ether, triethylene glycol dipropyl ether, triethylene glycol dibutyl ether, propylene glycol methyl ether, propylene glycol ethyl ether, propylene glycol-n-propyl ether, propylene glycol-n-butyl ether, dipropylene glycol methyl ether, dipropylene glycol ethyl ether, dipropylene glycol-n-propyl ether, dipropylene glycol-n-butyl ether, dipropylene glycol dimethyl ether, dipropylene glycol diethyl ether, dipropylene glycol dipropyl ether, dipropylene glycol dibutyl ether, tripropylene glycol methyl ether, tripropylene glycol ethyl ether, tripropylene glycol-n-propyl ether, tripropylene glycol-n-butyl ether, tripropylene glycol dimethyl ether, tripropylene glycol diethyl ether, tripropylene glycol dipropyl ether, tripropylene glycol dibutyl ether, and the like. One of the penetrants may be used alone or two or more of them may be used in combination.

A ratio of the penetrant (penetrant ratio) relative to the total amount of the ink is not particularly limited and is, for example, in the range of about 0 wt % to about 20 wt %. Setting of the penetrant ratio in the aforementioned range makes it possible to obtain suitable penetration of the water-based ink relative to a recording medium such as a recording paper. The penetrant ratio may be in the range of about 0.1 wt % to about 15 wt %, and in the range of about 0.5 wt % to about 10 wt %.

The luminescence marker is not particularly limited and examples thereof include luminol (5-amino-2,3-dihydro-1,4-phthalazinedione, Chemical Formula (1)), lucigenin (bis-N-methylacridinium nitrate salt (I), Chemical Formula (2)), and the like. One of the luminescence markers may be used alone or two or more of them may be used in combination.

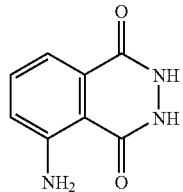

(1)

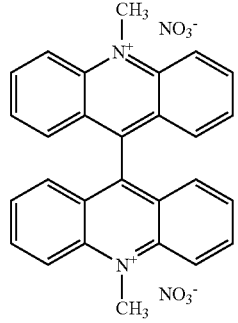

(2)

Considering luminescence intensity, solubility of the luminescence marker to the ink, and the like, a ratio of the luminescence marker relative to the total amount of the ink may be in the range of about 0.01 wt % to about 0.5 wt %, in the range of about 0.05 wt % to about 0.2 wt %, and in the range of about 0.1 wt % to about 0.2 wt %.

pH of the ink for ink-jet recording may be in the range of about 7 to about 12, and in the range of about 8 to about 10. Particularly, considering solubility of the luminescence marker to the ink, pH of the ink may be at about 8 or more. In order to adjust pH in the aforementioned desired range, the ink for ink-jet recording may comprise a pH adjuster. Examples of the pH adjuster include alkali metal hydroxide such as sodium hydroxide, potassium hydroxide, lithium hydroxide, and the like; lower alkanolamine such as ethanolamine, diethanolamine, triethanolamine, propanolamine, and the like; ammonium hydroxide; monobasic potassium phosphate; and the like. An amount of the pH adjuster may suitably be adjusted according to pH of the desired ink.

The ink for ink-jet recording may be a clear ink that does not comprise a coloring agent or a colored ink that comprises the coloring agent. The coloring agent to be comprised in the colored ink is preferably a dye because it does not generate aggregation and luminescence thereof may easily be confirmed. However the present invention is not limited thereto and the coloring agent may be a pigment. Further, as the coloring agent, a mixture of a dye and a pigment may be used.

The dye is not particularly limited and examples thereof include a direct dye, an acid dye, a basic dye, a reactive dye, and the like. Specific Examples of the dye include C. I. Direct Black, C. I. Direct Blue, C. I. Direct Red, C. I. Direct Yellow, C. I. Direct Orange, C. I. Direct Violet, C. I. Direct Brown, C. I. Direct Green, C. I. Acid Black, C. I. Acid Blue, C. I. Acid Red, C. I. Acid Yellow, C. I. Acid Orange, C. I. Acid Violet, C. I. Basic Black, C. I. Basic Blue, C. I. Basic Red, C. I. Basic Violet, C. I. Food Black, and the like. Examples of the C. I. Direct Black include C. I. Direct Black 17, 19, 32, 51, 71, 108, 146, 154, 168, and the like. Examples of the C. I. Direct Blue include C.I. Direct Blue 6, 22, 25, 71, 86, 90, 106, 199, and the like. Examples of the C. I. Direct Red include C. I. Direct Red 1, 4, 17, 28, 83, 227, and the like. Examples of the C. I. Direct Yellow include C. I. Direct Yellow 12, 24, 26, 86, 98, 132, 142, 173, and the like. Examples of the C. I. Direct Orange include C. I. Direct Orange 34, 39, 44, 46, 60, and the like. Examples of the C. I. Direct Violet include C. I. Direct Violet 47, 48, and the like. Examples of the C. I. Direct Brown include C. I. Direct Brown 109, and the like. Examples of the C. I. Direct Green include C. I. Direct Green 59, and the like. Examples of the C. I. Acid Black include C. I. Acid Black 2, 7, 24, 26, 31, 52, 63, 112, 118, and the like. Examples of the C. I. Acid Blue include C. I. Acid Blue 9, 22, 40, 59, 93, 102, 104, 117, 120, 167, 229, 234, and the like. Examples of the C. I. Acid Red include C. I. Acid Red 1, 6, 32, 37, 51, 52, 80, 85, 87, 92, 94, 115, 180, 256, 289, 315, 317, and the like. Examples of the C. I. Acid Yellow include C. I. Acid Yellow 11, 17, 23, 25, 29, 42, 61, 71, and the like. Examples of the C. I. Acid Orange include C. I. Acid Orange 7, 19, and the like. Examples of the C. I. Acid Violet include C. I. Acid Violet 49, and the like. Examples of the C. I. Basic Black include C. I. Basic Black 2, and the like. Examples of the C. I. Basic Blue include C. I. Basic Blue 1, 3, 5, 7, 9, 24, 25, 26, 28, 29, and the like. Examples of the C. I. Basic Red include C. I. Basic Red 1, 2, 9, 12, 13, 14, 37, and the like. Examples of the C. I. Basic Violet include C. I. Basic Violet 7, 14, 27, and the like. Examples of the C. I. Food Black include C. I. Food Black 1, 2, and the like. These dyes are excellent in characteristics such as, vividness, water solubility, and stability.

A ratio of the dye (dye ratio) relative to the total amount of the ink is not particularly limited and is, for example, in the range of about 0.1 wt % to about 20 wt %. The dye ratio may be 20 wt % or more as long as the ink for ink-jet recording is stable and precipitate is not generated in the ink. One of the dyes may be used alone or two or more of them may be used in combination.

The pigment is not particularly limited. For example, carbon black, an inorganic pigment, and an organic pigment may be used. Examples of the carbon black include furnace black, lamp black, acetylene black, channel black, and the like. Examples of the inorganic pigment include titanium oxide, iron oxide inorganic pigment, and carbon black inorganic pigment, and the like. Examples of the organic pigment include an azo pigment such as azo lake, an insoluble azo pigment, a condensed azo pigment, a chelate azo pigment; a polycyclic pigment such as a phthalocyanine pigment, a perylene and perynone pigment, an anthraquinone pigment, a quinacridone pigment, a dioxazine pigment, a thioindigo pigment, an isoindolinone pigment, a quinophthalone pigment, and the like; a dye lake pigment such as a basic dye lake pigment, an acid dye lake pigment, and the like; a nitro pigment; a nitroso pigment; an aniline black daylight fluorescent pigment; and the like. Further other pigments may be used as long as they are dispersible to an aqueous phase. Examples of the pigments include C. I. Pigment Black 1, 6, and 7; C. I. Pigment Yellow 1, 2, 3, 12, 13, 14, 15, 16, 17, 55, 73, 74, 75, 83, 93, 94, 95, 97, 98, 114, 128, 129, 138, 150, 151, 154, 180, 185, and 194; C. I. Pigment Orange 31 and 43; C. I. Pigment Red 2, 3, 5, 6, 7, 12, 15, 16, 48, 48:1, 53:1, 57, 57:1, 112, 122, 123, 139, 144, 146, 149, 166, 168, 175, 176, 177, 178, 184, 185, 190, 202, 221, 222, 224, and 238; C. I. Pigment Violet 196; C. I. Pigment Blue 1, 2, 3, 15, 15:1, 15:2, 15:3, 15:4, 16, 22, and 60; C. I. Pigment Green 7 and 36; and the like.

A ratio of the pigment (pigment ratio) relative to the total amount of the ink is not particularly limited and may be decided suitably according to desired printing density, color, and the like. The pigment ratio is, for example, in the range of about 0.5 wt % to about 20 wt %, and in the range of about 0.5 wt % to about 15 wt %. Particularly, considering easiness of confirmation of luminescence, the pigment ratio may be in the range of about 0.5 wt % to about 10 wt %, and in the range of about 0.5 wt % to about 3 wt %. One of the pigments may be used alone or two or more of them may be used in combination.

In a case where the ink for ink-jet recording comprises the pigment, a dispersant may be added to the ink as required. The dispersant is not particularly limited. For example, high-molecular-weight polyurethane; polyester; polymeric copolymer containing functional group showing strong affinity to a pigment of carbonyl group or amino group; and the like are preferable.

The ink for ink-jet recording further may comprise a conventionally known additive as required. Examples of the additive include a surfactant, a viscosity modifier, a surface tension modifier, and a mildewproofing agent. Examples of the viscosity modifier include, without limitation, polyvinyl alcohol, polyvinylpyrrolidone, cellulose, water-soluble resin, and the like.

The ink for ink-jet recording is produced by uniformly mixing the luminescence marker with other added components, and then removing insolubles with a filter, for example. A method of producing the ink for ink-jet recording is, for example, as follows.

In the method of producing the ink for ink-jet recording, pH of aqueous solution comprising the luminescence marker is adjusted at about 8 or more. Then, components of the ink are added to the aqueous solution and mixed. The components of the ink are, for example, the water-soluble organic solvent, the coloring agent, and the like. An example of a method of adjusting pH at about 8 or more includes a method of adding alkaline substance. Examples of alkaline substance include sodium hydroxide, potassium hydroxide, lithium hydroxide, and solution thereof. Further, in order to stabilize a condition of pH at about 8 or more, a buffering agent or a buffer solution is preferably used. As the buffering agent and the buffer solution, conventionally known buffering agent and buffer solution may be used. For example, triethanolamine is preferable. Other conditions are as same as explained in the case of the ink for ink-jet recording. In this manner, by adjusting pH of water comprising the luminescence marker at about 8 or more, the luminescence marker becomes easy to dissolve and luminescence because of oxidation of the luminescence marker in accordance with decrease in pH may be prevented.

With respect to the ink for ink-jet recording, the luminescence marker is used for determining whether the ink is used for recording the ink-jet recorded object. Therefore, unlike a case where the conventional fluorescence substance, which emits light due to irradiation of an ultraviolet ray or a near-infrared ray, is used as a marker, it may be determined whether the ink is used for recording the ink-jet recorded object with a simple method such as an evaluation of luminescence by oxidation, without requiring a special equipment such as an ultraviolet ray lamp, near-infrared ray light-emitting diode, a power supply unit, and the like.

Further, luminescence by oxidation of the luminescence marker is rarely affected by temperature change. Therefore, unlike a case where a compound, which emits light by enzyme reaction, is used as a marker, with respect to the ink for ink-jet recording, the determination may be performed at any time regardless of the temperature change.

The ink cartridge is explained. As described above, the ink cartridge comprises an ink for ink-jet recording, and the ink is the ink for ink-jet recording comprising the luminescence marker. As a body of the ink cartridge, for example, a conventionally known body may be used.

The ink-jet recording apparatus is explained. The ink-jet recording apparatus comprises an ink storing portion and an ink ejecting unit, and an ink stored in the ink storing portion is ejected by the ink ejecting unit. The ink cartridge is stored in the ink storing portion. Other than this, the ink-jet recording apparatus may have the construction similar to that of a conventionally known ink-jet recording apparatus.

FIG. 1 shows a construction of an example of the ink-jet recording apparatus. As shown in FIG. 1, the ink-jet recording apparatus 1 comprises five ink cartridges 2, an ink-jet head 3, a head unit 4, a carriage 5, a drive unit 6, a platen roller 7, and a purge unit 8 as main constructional elements. In the ink-jet recording apparatus 1, the ink-jet head 3 is the ink ejecting unit.

The five ink cartridges 2 each comprise colored inks of yellow, magenta, cyan, and black, and a clear ink. At least one of the five inks is the ink for ink-jet recording. The ink-jet head 3 performs recording on a recording medium P such as a recording paper. The head unit 4 is provided with the ink jet head 3. The five ink cartridges 2 and the head unit 4 are mounted to the carriage 5. The drive unit 6 reciprocates the carriage 5 in a straight line. The platen roller 7 extends in a reciprocating direction of the carriage 5 and opposes to the ink-jet head 3.

The drive unit 6 comprises a carriage shaft 9, a guide plate 10, a pair of pulleys 11 and 12, and an endless belt 13. The carriage shaft 9 is disposed at a lower end portion of the carriage 5 and extends in parallel to the platen roller 7. The guide plate 10 is disposed at an upper end portion of the carriage 5 and extends in parallel to the carriage shaft 9. The pulleys 11 and 12 are disposed in positions corresponding to both end portions of the carriage shaft 9 and between the carriage shaft 9 and the guide plate 10. The endless belt 13 is stretched between the pulleys 11 and 12.

In the ink-jet recording apparatus 1, as the pulley 11 is rotated in normal and reverse directions by the drive of a carriage motor 101, the carriage 5 which is connected to the endless belt 13 is reciprocated linearly along the carriage shaft 9 and the guide plate 10 in accordance with the rotation of the pulley 11.

Figure 2:
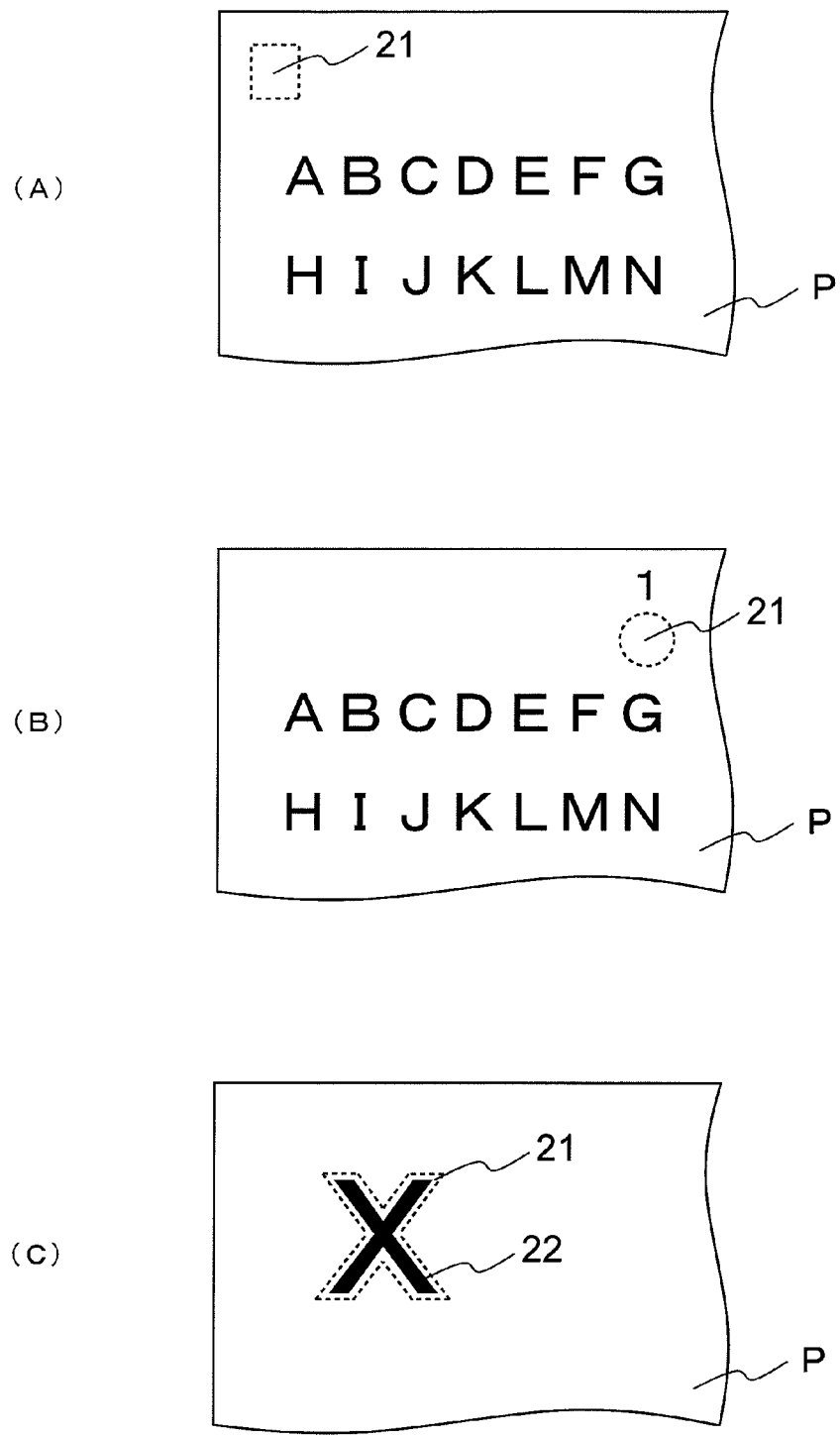
FIG. 2(A) to (C) are views showing a construction of examples of the determining part.

The recording medium P is fed from a paper feeding cassette (not shown) positioned on a side of or underneath the ink-jet recording apparatus 1. The recording medium P is introduced between the ink-jet head 3 and the platen roller 7. Then, a predetermined recording is performed on the recording medium P with the ink ejected from the ink-jet head 3. For example, in a case where the black ink is the ink for ink-jet recording, the ink for ink-jet recording is used for a black recording part. In contrast, for example, in a case where the clear ink is the ink for ink-jet recording, a determining part may be formed on a part different from the aforementioned recording part by ejecting the clear ink, or a determining part may be formed on the aforementioned recording part by overstriking the clear ink. A position where the determining part is formed is not particularly limited. However, the determining part is preferably formed on a preliminarily defined position. The determining part may automatically be formed on the predetermined position. Shape of the determining part is not particularly limited. The determining part may have arbitrary shape such as square, circle, ellipse, triangle, and the like. FIG. 2 shows a construction of examples of the determining part. For example, as shown in FIG. 2(A), the determining part 21 may be formed at a corner of the recording medium P in a shape of square. Further, for example, as shown in FIG. 2(B), the determining part 21 may be formed under a recording part of the page number of the recording medium P in a shape of circle. Still further, for example, as shown in FIG. 2(C), the determining part 21 may be formed around a recording part 22 recorded as letter and graphic. The recording medium P then is discharged from the ink-jet recording apparatus 1. In FIG. 1, a feeding mechanism and a discharging mechanism of the recording medium P are not shown.

The purge unit 8 is provided on a side of the platen roller 7. The purge unit 8 is disposed so as to oppose the ink-jet head 3 when the head unit 4 is in a reset position (above the purge unit 8 in this example). The purge unit 8 comprises a purge cap 14, a pump 15, a cam 16, and an ink reservoir 17. The purge cap 14 covers a plurality of nozzles (not shown) of the ink-jet head 3 when the head unit 4 is in a reset position. In this state, the pump 15 draws poor ink containing, for example, air bubbles trapped inside the ink-jet head 3, by being driven by the cam 16. Thereby, a recovery of the ink-jet head 3 is promoted. The drawn poor ink is stored in the ink reservoir 17.

A wiper member 20 is provided on the platen roller 7 side of the purge unit 8. The wiper member 20 has a spatula shape, and wipes a nozzle surface of the ink-jet head 3 in accordance with the movement of the carriage 5. In FIG. 1, the cap 18 covers the plurality of nozzles of the ink-jet head 3 that returns to the reset position after the completion of recording in order to prevent the ink from drying.

With respect to the ink-jet recording apparatus 1 of this example, the five ink cartridges 2 are mounted to one carriage 5. However, the present invention is not limited thereto. With respect to the ink-jet recording apparatus, the five ink cartridges may be mounted to a plurality of carriages. Further, the five ink cartridges may not be mounted to the carriage, but may be provided and fixed in the ink-jet recording apparatus. In this state, for example, the ink cartridge and the head unit mounted to the carriage are connected via a tube, or the like, and the ink is supplied to the head unit from the ink cartridge.

The first method of determining is explained. As described above, the first method of determining is a method of determining an ink for ink-jet recording used for recording an ink-jet recorded object. The determination determines whether the ink is the ink for ink-jet recording comprising the luminescence marker. A whole or a part of a recording part of the ink-jet recorded object (hereinafter, also may simply be referred to as "recording part") is oxidized. In a case where the recording part emits light by oxidation, it is determined that the ink is the ink for ink-jet recording comprising the luminescence marker. In a case where the recording part does not emit light by oxidation, it is determined that the ink is not the ink for ink-jet recording comprising the luminescence marker.

The part of the recording part is not particularly limited and examples thereof include a whole or a part of letter and graphic, a part where the page number is recorded, a whole or a part of a header or footer.

A method of evaluating luminescence is not particularly limited and examples thereof include a visual evaluation, an evaluation with an optical measuring instrument, and the like.

In the visual evaluation, the recording part is oxidized in a dark room where outside light is cut off, and the luminescence is visually evaluated.

Another example of the visual evaluation is as follows. That is, first, the ink-jet recorded object is placed on a light-impermeable substrate. Then, the recording part is covered with a light-resistant tube having an inner diameter of several cm to make a condition which is rarely affected by outside light. Next, the recording part is oxidized, and the luminescence is visually evaluated from an upper side of the light-resistant tube.

In the evaluation with the optical measuring instrument, for example, the recording part is oxidized, and the luminescence is automatically evaluated with a Charge Coupled Device (CCD), a photomultiplier tube, a photo sensor, a sensitive film, and the like. According to the present invention, a method of determining, in which the recording part is automatically evaluated with the optical measuring instrument, is provided. Thereby, even with respect to weak luminescence, it may automatically be evaluated regardless of an effect of outside light.

The first method of determining further includes determination of whether the recording part is already oxidized. In a case where the recording part is already oxidized, it may be determined that it is already determined whether the ink is the ink for ink-jet recording comprising the luminescence marker. In a case where the recording part is unoxidized, it may be determined that it is undetermined whether the ink is the ink for ink-jet recording comprising the luminescence marker. Once the recording part is oxidized, the recording part never emits light again by the oxidation. Therefore, in a case of already oxidized, by determining that it is already determined whether the ink is the ink for ink-jet recording comprising the luminescence marker, the determination is not idly repeated, and the efficient determination may be performed. For example, in a case where the recording part is wet with solution comprising oxidant described later, it may be determined that the recording part is already oxidized. Further, with respect to the first method of determining, unlike a case where the conventional fluorescence substance, which emits light due to irradiation of an ultraviolet ray or a near-infrared ray, is used as a marker, once the recording part is oxidized, a third party cannot freely determine whether the ink used for recording the ink-jet recorded object is the ink for ink-jet recording comprising the luminescence marker.

In the first method of determining, the luminescence marker of the ink for ink-jet recording may comprise at least one of luminol and lucigenin.

In the first method of determining, the oxidation may be an oxidation using an oxidant. The oxidant is not particularly limited and may be selected suitably according to types of the luminescence marker. Considering easiness of handling and obtainment, sodium hypochlorite, hydrogen peroxide, and the like may be used. Preferable examples of a method of oxidizing using the oxidant include a method of dropping solution comprising the oxidant on the recording part with a dropper, a method of impregnating solution comprising the oxidant to an absorbent member and then applying the solution to the recording part, and the like. The absorbent member is not particularly limited and examples thereof include cotton swab (for example, Q-tip® manufactured by Unilever), absorbent cotton, tissue paper, sponge, and the like. A concentration of the oxidant in the solution comprising the oxidant is not particularly limited as long as the luminescence marker contained in the recording part is emitted. The concentration of the oxidant in the solution comprising the oxidant is, for example, in the range of about 5 w/v % to about 30 w/v %.

Other conditions of the first method of determining are similar to that of the ink for ink-jet recording.

In the first method of determining, it is determined whether the ink used for recording the ink-jet recorded object is the ink for ink-jet recording on the basis of whether the recording part emits light when it is oxidized. Therefore, with respect to the first method of determining, confirmation of luminescence is easier than a case in which determination is performed on the basis of whether the ink itself emits light when it is oxidized. Further, with respect to the first method of determining, for example, in a case in which determination is performed at the place different from the place where the recording is performed, determination may be performed only by bringing out the ink-jet recorded object, which is easy to carry, without bringing out the ink itself.

In the first method of determining, on the basis of luminescence, it is determined whether the ink used for recording the ink-jet recorded object is the ink for ink-jet recording. Therefore, with respect to the first method of determining, unlike determination on the basis of change in color of the recording part, determination may be performed without requiring information of to what color the recording part is turned into.

The method of ink-jet recording is explained. As described above, the method of ink-jet recording is a method of recording by ejecting ink by an ink-jet recording system relative to a recording medium. The ink comprises a clear ink comprising the luminescence marker. A determining part is formed by ejecting the clear ink on a part different from a recording part of the recording medium. The determining part is as described above.

The second method of determining is explained. As described above, the second method of determining is a method of determining an ink for ink-jet recording used for recording an ink-jet recorded object. The determination determines whether the clear ink used for forming the determining part of the recording medium recorded by the method of ink-jet recording is a clear ink comprising the luminescence marker. A whole or a part of the determining part of the recording medium (hereinafter, also may simply be referred to as "determining part") is oxidized. In a case where the determining part emits light by oxidation, it is determined that the clear ink is the clear ink comprising the luminescence marker. In a case where the determining part does not emit light by oxidation, it is determined that the clear ink is not the clear ink comprising the luminescence marker.

According to the second method of determining, by using the clear ink for forming the determining part, it may be determined whether the ink used for forming the determining part is the ink for ink-jet recording without a third party knowing about that. Further, with respect to the second method of determining, in the determination, the determining part formed at a part different from the recording part of the recording medium is oxidized and the recording part is not damaged.

The second method of determining further comprises determination of whether the determining part is already oxidized. In a case where the determining part is already oxidized, it may be determined that it is already determined whether the ink is the clear ink comprising the luminescence marker. In a case where the determining part is unoxidized, it may be determined that it is undetermined whether the ink is the clear ink comprising the luminescence marker.

In the second method of determining, the luminescence marker of the clear ink may comprise at least one of luminol and lucigenin.

In the second method of determining, the oxidization may be an oxidization using an oxidant.

In the second method of determining, the oxidant may be at least one of sodium hypochlorite and hydrogen peroxide.

Other conditions of the second method of determining are similar to that of the ink for ink-jet recording and the first method of determining.

EXAMPLES

Examples of the present invention are described, which are provided for illustrative purposes only. The present invention is not limited by the following Examples.

Examples 1 to 7 and Controls 1 to 3

The ink for ink-jet recording of Examples 1 to 5 and Controls 1 to 3 comprising the dye as the coloring agent, and the ink for ink-jet recording of Example 7 not comprising the coloring agent were obtained as follows. That is, first, ink composition components (Table 1 to 3) were uniformly mixed. Thereafter, the mixture was filtered with a hydrophilic polytetrafluoroethylene (PTFE) type membrane filter having a pore diameter of 0.2 μm manufactured by ToyoRoshi Kaisha, Ltd. to produce each ink and thereby obtained the inks. Further, the ink for ink-jet recording of Example 6 comprising the pigment as the coloring agent was obtained as follows. That is, first, ink composition components (Table 2) were uniformly mixed. Thereafter, the mixture was filtered with a cellulose acetate type membrane filter having a pore diameter of 1.0 μm manufactured by ToyoRoshi Kaisha, Ltd. to produce the ink, and thereby obtained the ink.

With respect to each ink of Examples and Controls, a luminescence evaluation was carried out as follows.

(Luminescence Evaluation)

An ink cartridge was filled up with the ink of each Example and Control. Next, the ink cartridge was attached to a digital multi-function center DCP-330C, which mounted an ink-jet printer, manufactured by Brother Industries, Ltd. Then, a recording part for the luminescence evaluation was formed by printing a solid image on a plain paper PB PAPER manufactured by CANON INC. Thereafter, in a dark room, a cotton swab impregnated with sodium hypochlorite solution (sodium hypochlorite concentration 5 w/v %) or hydrogen peroxide solution (hydrogen peroxide concentration 5 w/v %) was applied to the recording part, and the luminescence at that time was visually evaluated in accordance with the following evaluation criteria.

Luminescence Evaluation Evaluation Criteria
AA: the recording part emitted extremely strong light
A: the recording part emitted strong light
B: the recording part emitted light
C: the recording part did not emit light Ink compositions, pH, and luminescence evaluation results of the ink of each Example are summarized in Tables 1 and 2. Further, ink compositions, pH, and luminescence evaluation results of the ink of each Control are summarized in Table 3.

TABLE 1

|  | Example 1 | Example 2 | Example 3 |
|---|---|---|---|
| INK COMPOSITION (wt %) |  |  |  |
| Glycerin | 25.0 | 25.0 | 25.0 |
| Triethylene glycol-n-butyl ether | 3.0 | 3.0 | 3.0 |
| Triethanol amine | 1.0 | 1.0 | 1.0 |
| luminol | 0.2 | 0.1 | — |
| lucigenin | — | — | 0.2 |
| C.I. Acid Blue 9 | 1.0 | — | 1.0 |
| C.I. Direct Yellow 132 | — | 1.0 | — |
| Water | Balance | Balance | Balance |
| pH of ink | 8.7 | 8.5 | 8.5 |
| LUMINESCENSE EVALUATION |  |  |  |
| Sodium hypochlorite solution | A | A | A |
| Hydrogen peroxide solution | A | A | A |

TABLE 2

|  | Example 4 | Example 5 | Example 6 | Example 7 |
|---|---|---|---|---|
| INK COMPOSITION (wt %) |  |  |  |  |
| Glycerin | 25.0 | 25.0 | 25.0 | 25.0 |
| Triethylene glycol-n-butyl ether | 3.0 | 3.0 | 3.0 | 3.0 |
| Triethanol amine | 0.2 | 1.0 | 1.0 | 1.0 |
| luminol | 0.1 | 0.05 | 0.1 | 0.1 |
| C.I. Acid Blue 9 | 1.0 | 1.0 | — | — |
| CAB-O-JET ® 270Y (1*) | — | — | 10.0 | — |
| Water | Balance | Balance | Balance | Balance |
| pH of ink | 7.7 | 8.6 | 8.6 | 8.8 |
| LUMINESCENSE EVALUATION |  |  |  |  |
| Sodium hypochlorite solution | B | B | B | AA |
| Hydrogen peroxide solution | B | B | B | AA |

(1*) manufactured by Cabot Specialty Chemicals, Inc., pigment solid content: 10 wt %

TABLE 3

|  | Control 1 | Control 2 | Control 3 |
|---|---|---|---|
| INK COMPOSITION (wt %) |  |  |  |
| Glycerin | 25.0 | 25.0 | 25.0 |
| Triethylene glycol-n-butyl ether | 3.0 | 3.0 | 3.0 |
| Triethanol amine | 1.0 | 1.0 | 1.0 |
| 4,4'-bis(2-methoxystyryl)biphenyl | 0.1 | — | — |
| 1,4-diazabicyclo-2,2,2-octane | — | 0.1 | — |
| C.I. Acid Blue 9 | 1.0 | — | 1.0 |
| C.I. Direct Yellow 132 | — | 1.0 | — |
| Water | Balance | Balance | Balance |
| pH of ink | 8.8 | 8.4 | 8.5 |
| LUMINESCENSE EVALUATION |  |  |  |
| Sodium hypochlorite solution | C | C | C |
| Hydrogen peroxide solution | C | C | C |

As shown in Tables 1 and 2, each ink of Examples 1 to 3, and Example 7 not comprising the coloring agent were good in the result of the luminescence evaluation. The ink of Example 4, pH of which was 7.7, was slightly inferior in the result of the luminescence evaluation as compared to each ink of Examples 1 to 3, however was a reasonable level in practical use. The ink of Example 5, the ratio of the luminescence marker (luminol) relative to a total amount of the ink was 0.05 wt %, was slightly inferior in the result of the luminescence evaluation as compared to each ink of Examples 1 to 3, however was a reasonable level in practical use. The ink of Example 6 comprising the pigment as the coloring agent was slightly inferior in the result of the luminescence evaluation as compared to each ink of Examples 1 to 3, however was a reasonable level in practical use. In contrast, as shown in Table 3, with respect to the ink of Control 1 to which a fluorescence substance that emits light due to irradiation of an ultraviolet ray was added instead of the luminescence marker, the ink of Control 2 to which a color fading inhibitor was added, and the ink of Control 3 to which none of them were added, the recording part did not emit light at all even when the recording part was oxidized.

It will be obvious to those having skill in the art that many changes may be made in the above-described details of the particular aspects described herein without departing from the spirit or scope of the invention as defined in the appended claims.

What is claimed is:

1. A method of ink jet recording performing recording comprising the steps of:
    forming a recording part by ejecting a colored ink that comprises a coloring agent on a recording medium using an ink jet recording system;

forming a determining part by ejecting a clear ink that does not comprise the coloring agent on a part of the recording medium that is different from the recording part of the recording medium using the ink jet recording system, wherein the clear ink comprises a luminescence marker that emits light by oxidization and the luminescence marker is at least one of luminol and lucigenin;

oxidizing at least part of the determining part of the recording medium using an oxidant;

determining that the clear ink comprises the luminescence marker if the determining part of the recording medium emits light by oxidation; and determining that the clear ink does not comprise the luminescence marker if the determining part of the recording medium does not emit light by oxidation.

2. The method of ink jet recording according to claim 1, wherein a ratio of the luminescence marker relative to a total amount of the colored ink is in a range of about 0.01 wt % to about 0.5 wt %.

3. The method of ink jet recording according to claim 1, wherein pH of the colored ink is at about 8 or more.

4. The method of ink jet recording according to claim 1, wherein the colored ink is a water-based ink comprising water and water-soluble organic solvent.

5. The method of ink jet recording according to claim 1, further comprising the step of:

determining whether a whole or a part of the determining part is already oxidized, wherein:
in a case where the determining part is already oxidized, it is determined that it is already determined whether the colored ink ejected on the first part of the recording medium comprises the luminescence marker which emits light by oxidization, and in a case where the determining part is unoxidized, it is determined that it is undetermined whether the colored ink ejected on the first part of the recording medium comprises the luminescence marker which emits light by oxidization.

6. The method of ink jet recording according to claim 1, wherein the step of oxidizing a whole or a part of the determining part comprises oxidizing a whole or a part of the determining part using an oxidant.

7. The method of ink jet recording according to claim 1, wherein the luminescence marker is lucigenin.

* * * * *